United States Patent
Eacho et al.

(10) Patent No.: US 7,595,403 B2
(45) Date of Patent: Sep. 29, 2009

(54) BENZISOTHIAZOL-3-ONE-CARBOXYLIC ACID AMIDES AS PHOSPHOLIPASE INHIBITORS

(75) Inventors: Patrick Irving Eacho, Indianapolis, IN (US); Patricia Sue Foxworthy-Mason, Indianapolis, IN (US); Ho-Shen Lin, Indianapolis, IN (US); Jose Eduardo Lopez, Fishers, IN (US); Marian Kazimierz Mosior, Carmel, IN (US); Michael Enrico Richett, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/550,006

(22) PCT Filed: Mar. 25, 2004

(86) PCT No.: PCT/US2004/006094

§ 371 (c)(1),
(2), (4) Date: Sep. 14, 2005

(87) PCT Pub. No.: WO2004/094394

PCT Pub. Date: Nov. 4, 2004

(65) Prior Publication Data

US 2006/0276522 A1    Dec. 7, 2006

Related U.S. Application Data

(60) Provisional application No. 60/459,832, filed on Apr. 1, 2003.

(51) Int. Cl.
*A61K 31/428* (2006.01)
*C07D 275/04* (2006.01)

(52) U.S. Cl. ...................................... 548/209; 514/373
(58) Field of Classification Search .................. 548/209
See application file for complete search history.

(56) References Cited

U.S. PATENT DOCUMENTS

| 3,517,022 A | 6/1970 | Miller et al. |
| 5,856,503 A | 1/1999 | Aebi et al. |
| 5,998,463 A | 12/1999 | Hulin et al. |

FOREIGN PATENT DOCUMENTS

| EP | 0 506 532 A | 9/1992 |
| JP | 48 029134 B | 9/1973 |
| WO | WO 96/39384 | 12/1996 |

OTHER PUBLICATIONS

Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Choi et al., Journal of Lipid Research, vol. 43, 2002, pp. 1763-1769.*
An English translation of JP 48-029134, Sep. 7, 1973.*

* cited by examiner

*Primary Examiner*—Laura L. Stockton
(74) *Attorney, Agent, or Firm*—James B. Myers

(57) ABSTRACT

A novel class of benzisothiazole-3(2H)-one compounds is disclosed together with the use of such compounds for inhibiting hepatic lipase and/or endothelial lipase activity for treatment, amelioration or prevention of hepatic lipase and/or endothelial lipase mediated diseases. (I)

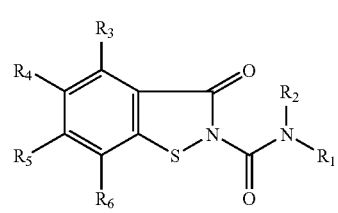

7 Claims, No Drawings

BENZISOTHIAZOL-3-ONE-CARBOXYLIC ACID AMIDES AS PHOSPHOLIPASE INHIBITORS

REFERENCE TO RELATED APPLICATIONS

This application is a United States national phase entry, pursuant to 35 U.S.C. 371, of PCT/US2004/006094, filed on Mar. 25, 2004, which claims the benefit of U.S. Provisional patent application Ser. No. 60/459,832, filed Apr. 1, 2003.

FIELD OF THE INVENTION

This invention relates to novel benzisothiazole-3(2H)-one compounds useful for the treatment and/or prevention of diseases mediated by phospholipases including hepatic lipase and endothelial lipase.

BACKGROUND OF THE INVENTION

Hepatic lipase plays an important role in lipid metabolism. Hepatic lipase is a glycoprotein that functions as a ligand or as an enzyme of approximately 65 Kda, which has been shown to catalyze the hydrolysis of lipids including triglycerides, diglycerides and phospholipids in native lipoproteins. It has also been shown to facilitate the selective uptake of cholesterol from high-density lipoproteins and the removal of remnant particles by the liver (Jonathan C. Cohen, et al *Biochemistry* 1992, 31: 8544-8551 and Neve et al *Biochemistry J.* 1998, 330:701-706).

Other studies showing the inverse relationship of HDL and hepatic lipase activity include for example, Haffner S. M. et al., "Studies on the metabolic mechanism of reduced high density lipoproteins during anabolic steroid therapy," *Metabolism* 1983; 32:413-420; Applebaum-Bowden D, et al., "The Dyslipoproteinemia of Anabolic steroid therapy: increase in hepatic triglyceride lipase precedes the decrease in high density lipoprotein-2 cholesterol," *Metabolism* 1987; 36:949-952; and Kantor M. A. et al., "Androgens reduce HDL-2 cholesterol and increase hepatic triglyceride lipase activity," *Med. Sci. Sport exercise* 1985; 17:462-465.

The inverse relationship between hepatic lipase activity and the level of HDL-cholesterol, particularly type-2 HDL-cholesterol, can be used to advantage in up-regulating the Level of HDL cholesterol-the good cholesterol.

Endothelial lipase (EL) is a newly described member of the lipase gene family. Like hepatic lipase, endothelial lipase has been implicated in the hydrolysis of HDL phospholipids and in the reduction of HDL-cholesterol in vivo.

In experiments using hepatic lipase knockout mice the infusion of a polyclonal antibody inhibitory to endothelial lipase resulted in a marked increase in HDL-cholesterol levels (Rader, D. J., et al *Journal of Clinical Investigation* (2003), 111(3) 357-362.

Chan, et al, *Proceedings of the National Academy of Sciences* U.S.A. (2003), 100(5), 2748-2753, has also reported the inverse relation between endothelial lipase and HDL-cholesterol.

Given the preceding information, it is desirable to discover and develop compounds that increase HDL levels by methods that may include inhibiting the activity of hepatic lipase and/or endothelial lipase in order to treat, prevent and/or ameliorate the effects of hepatic lipase and/or endothelial lipase mediated diseases. Few therapeutically desirable agents are available to accomplish the task of increasing HDL levels hence the need for and utility of the present invention.

SUMMARY OF THE INVENTION

The present invention provides a compound of formula (I) or a pharmaceutically acceptable salt, enantiomer, solvate or prodrug thereof, for the treatment, amelioration and/or prevention of diseases mediated by hepatic lipase and/or endothelial lipase activity:

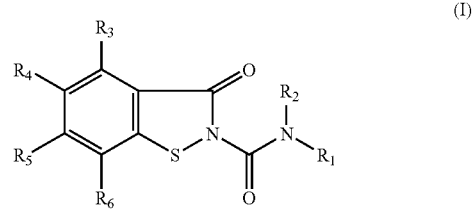

(I)

wherein;

$R_1$ is the group $(C_5-C_{12})$alkyl, $(C_4-C_{12})$haloalkyl, $(C_4-C_{12})$alkenyl, $(C_4-C_{12})$alkynyl, $(C_1-C_8)$alkylcycloalkyl, $(C_3-C_8)$cycloalkyl, $(C_1-C_{12})$alkylheterocyclic radical or aryl wherein the aryl or heterocyclkic group is optionally substituted with one 1 to 3 groups independently selected from $(C_1-C_{12})$alkyl, $(C_2-C_{12})$alkenyl, $(C_1-C_{12})$alkoxy, $(C_1-C_8)$alkylcycloalkyl, halo, and $(C_1-C_{12})$haloalkyl;

$R_2$ is hydrogen;

$R_3$, $R_4$, $R_5$, and $R_6$, are each independently selected from hydrogen, $(C_2-C_{12})$alkyl, $(C_1-C_{12})$haloalkyl, $(C_1-C_{12})$alkoxyalkyl, $(C_1-C_{10})$thioalkyl, hydroxy, $(C_2-C_{12})$alkenyl, $(C_2-C_{12})$alkynyl, $(C_1-C_{12})$alkylaryl, $(C_1-C_{12})$alkylcycloalkyl, $(C_1-C_{12})$alkylheterocyclic, $C(O)C_1-C_6$ alkyl $C(O)OC_1-C_6$alkyl, phenyl or aryl; wherein each of alkyl, alkenyl, phenyl or aryl groups may be optionally substituted with one to three substitutents selected from halo, amino, halo, $C_1-C_6$ alkyl, $(C_2-C_6)$alkennyl, $(C_1-C_6)$haloalkyl; or a pharmaceutically acceptable salt, solvate or isomer thereof.

The present invention provides novel benzoisothiazole-3 (2H)-one compounds of formula I having potent and selective effectiveness as inhibitors of mammalian hepatic lipase and/or endothelial lipase.

The present invention also relates to the use of compounds of formula I

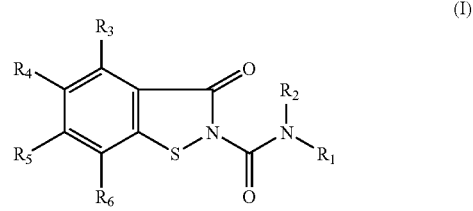

(I)

wherein;

$R_1$ is the group $(C_5-C_{12})$alkyl, $(C_4-C_{12})$haloalkyl, $(C_4-C_{12})$alkenyl, $(C_4-C_{12})$alkynyl, $(C_1-C_8)$alkylcycloalkyl, $(C_3-C_8)$cycloalkyl, $(C_1-C_{12})$alkylheterocyclic radical or aryl wherein the aryl or heterocyclkic group is optionally substituted with one 1 to 3 groups independently selected from $(C_1-C_{12})$alkyl, ($C_2$-$C_{12}$)alkenyl, ($C_1$-$C_{12}$)alkoxy, ($C_1$-$C_8$)alkylcycloalkyl, halo, and ($C_1$-$C_{12}$)haloalkyl;

$R_2$ is hydrogen;

$R_3$, $R_4$, $R_5$, and $R_6$, are each independently selected from hydrogen, ($C_2$-$C_{12}$)alkyl, ($C_1$-$C_{12}$)haloalkyl, ($C_1$-$C_{12}$)alkoxyalkyl, ($C_1$-$C_{10}$)thioalkyl, hydroxy, ($C_2$-$C_{12}$)alkenyl, ($C_2$-$C_{12}$)alkynyl, ($C_1$-$C_{12}$)alkylaryl, ($C_1$-$C_{12}$)alkylcycloalkyl, ($C_1$-$C_{12}$)alkylheterocyclic, C(O)$C_1$-$C_6$ alkyl, C(O)O$C_1$-$C_6$alkyl, phenyl or aryl; wherein each of alkyl, alkenyl, phenyl or aryl groups may be optionally substituted with one to three substitutents selected from halo, amino, halo, $C_1$-$C_6$ alkyl, ($C_2$-$C_6$)alkennyl, ($C_1$-$C_6$)haloalkyl; or a pharmaceutically acceptable salt, solvate or isomer thereof, for the treatment and/or prevention of hepatic lipase and/or endothelial lipase-mediated diseases.

The present invention also relates to the use of a novel benzisothiazole-3(2H)-one compound of formula I to increase or mediate the increase of high-density lipoproteins (HDL) upon administration to a patient in need thereof.

The present invention provides a pharmaceutical composition containing any of the compounds of the formula I.

The present invention also relates to the use of a pharmaceutical formulation comprising a compound of formula I and a carrier and/or diluent for the treatment and/or prevention of hypercholesterolemia.

The present invention relates to the use of a pharmaceutical composition comprising a therapeutically effective amount of a compound of formula I and mixtures thereof for the manufacture of a medicament for the treatment of hepatic lipase and/or endothelial lipase-mediated diseases.

DEFINITIONS

The terms "mammal" and "mammalian" include human and domesticated quadrupeds.

The phrase, "hepatic lipase and/or endothelial lipase mediated-diseases" refers to diseases symptomatic of low HDL levels, caused by, modulated by, exacerbated by or induced directly or indirectly by elevated hepatic lipase and/or endothelial lipase activity, and include for example, hypercholesterolemia, hyperlipidemia, stroke, hypertriglyceridemia, atherosclerosis and related diseases. Treatment and/or prevention of such diseases comprises administering to a mammal in need of such treatment a therapeutically effective amount of the compound of formula I in an amount sufficient to inhibit, ameliorate and/or prevent hepatic lipase and/or endothelial lipase activity and to thereby inhibit or prevent the deleterious effects of hepatic lipase and/or endothelial lipase activity.

The term "Active Ingredient" as used herein refers to a compound(s) of Formula (I) or a pharmaceutically acceptable salt, solvate, prodrug, racemate or enantiomer thereof either as the pure compound or delivered as a pharmaceutical formulation or a pharmaceutical composition. The pharmaceutical composition or formulation containing a compound of the invention and other compound(s) or treatment regimens useful for the treatment and/or prevention of diseases associated with or exacerbated by hepatic lipase and/or endothelial lipase activity (combination drugs) are contemplated to be within the meaning of the term "Active Ingredient(s)."

The term "benzisothiazole-3(2H)-one", or "benzisothiazole-3(2H)-one nucleus" as used herein refers to a nucleus with the structural formula (X):

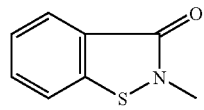

The benzisothiazole-3(2H)-one compounds of the invention employ certain defining terms as follows:

The term "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term "halo" means fluoro, chloro, bromo, or iodo.

The term "heterocyclic radical" or "heterocyclic group" refers to radicals derived from monocyclic or polycyclic, saturated or unsaturated, substituted or unsubstituted heterocyclic nuclei having 5 to 12 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b)thiophenyl, carbazolyl, norharmanyl, azabenzo(b)thiophenyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The terms "$C_1$-$C_{12}$alkylcyclopentyl," "$C_1$-$C_{12}$alkylcyclohexyl," or "$C_1$-$C_{12}$alkylheterocyclic" represent respectively a $C_1$-$C_{12}$alkyl, $C_1$-$C_{12}$alkyl, or $C_1$-$C_{12}$alkyl attached to a cylopentyl, cyclohexyl, and heterocyclic group respectively, wherein the entire group is attached to the dihydro-1H-indazole nucleus (X) or other substrate via the alkyl terminus at indicated or designated positions. The term "cycloalkyl" or "($C_3$-$C_8$)cycloalkyl" without more implies a cycloalkyl group having from 3 to 8 carbon atoms.

The term "substituted group" is an organic group substituted with one or more suitable substituents. For example, substituted plienyl as used herein refers to a phenyl group having one to three substituents selected from $C_1$-$C_{12}$alkyl, $C_2$-$C_{12}$haloalkyl, $C_2$-$C_{12}$alkenyl, $C_2$-$C_{12}$alkynyl, $C_2$-$C_{12}$alkylaryl, $C_1$-$C_{12}$alkylcyclohexyl, $C_1$-$C_{12}$alkylcyclopentyl, $C_1$-$C_{12}$alkylheterocyclic, $(CH_2)_m$COOH, $(CH_2)_m$CO($C_1$-$C_{10}$)alkyl, $(CH_2)_m$COO($C_1$-$C_{10}$)alkyl, $(CH_2)_m$COO($C_1$-$C_{10}$)alkylaryl, $C_1$-$C_{10}$alkylamino, halo, $(CH_2)_m$CONH$_2$, $(CH_2)_m$CON((C1-C6)alkyl)$_2$, phenyl, substituted phenyl, or aryl, wherein m=0, 1, 2, or 3. Similarly, the term substituted benzyl means a benzyl group ($CH_2$Phenyl) having substitution on the phenyl ring as described above. Analogously, the term aryl as used herein has its usual meaning and especially refers to the benzyl group.

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the benzisothiazole-3(2H)-one nucleus have been drawn to show the first line as a connecting bond only. Thus, the group

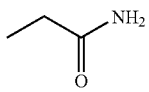

represents the acetamide radical or group, not the propanamide radical unless otherwise indicated.

The term, "alkylene chain of 1 or 2 carbon atoms" refers to the divalent radicals, —$CH_2$—$CH_2$— and —$CH_2$—.

The benzisothiazole-3(2H)-one Compounds of the Invention

The present invention provides the use of a novel class of benzisothiazole-3(2H)-one compounds useful as inhibitors of hepatic lipase and/or endothelial lipase activity for the treatment, amelioration and/or prevention of hepatic lipase and/or endothelial lipase-mediated diseases.

Preferred Subgroups of Compounds of Formula (I)

Preferred $R_1$ substituents:

The preferred group for $R_1$ is a substituted or unsubstituted group selected from the group consisting of ($C_5$-$C_{12}$)cycloalkyl, ($C_5$-$C_{12}$)cycloalkenyl, cycohexylmethyl, cyclopentylmethyl, cyclohexylethyl, phenyl, benzyl, naphthyl, norbornanyl, bicycloheptadienyl, toluyl, xylenyl, indenyl, stilbenyl, indolyl, bizothiophenyl, terphenylyl, diphenylethylenyl, phenylcyclohexenyl, acenaphthylenyl, and anthracenyl, biphenyl, bibenzylyl and related bibenzylyl homologues represented by the formula (a);

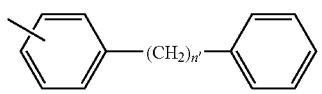

(a)

where n' is a number from 1 to 8.

A more preferred as the group $R_1$ is a group selected from the group consisting of pentyl, isopentyl, cyclohexylmethyl, cycloheptylmethyl, phenyl and benzyl, 1,5-disubstituted benzyl, 3,5-disubstituted benzyl and 2,4-disubstitued benztl. Preferred as the substitutent on the benzyl ring are independently, methyl, ethyl, propyl, isopropyl, butyl, isobutyl, tert-butyl, pentane, cyclohexane, cyclopentane, methylcyclohexyl and methylcylopentyl.

Preferred $R_3$, $R_4$, $R_5$, and $R_6$ substituents:

$R_3$, $R_4$, $R_5$, and $R_6$ are preferably independently selected from the group consisting of hydrogen, ($C_1$-$C_4$)alkyl, ($C_2$-$C_4$)alkenyl, —O—(($C_1$-$C_4$)alkyl), COOH, C(O)$C_1$-$C_6$ alkyl, C(O)O$C_1$-$C_6$alkyl, —S—(($C_1$-$C_3$)alkyl), —($C_5$-$C_{12}$)cycloalkyl, —$CF_3$, halo, —$NO_2$, —CN, —$SO_3$. Also preferred are $R_3$, $R_4$, $R_5$, and $R_6$ selected from $C_6$-$C_{12}$)alkylcyclopentyl, ($C_1$-$C_{12}$)alkylcyclohexyl," or "($C_1$-$C_{12}$)alkylheterocyclic" group. Particularly preferred $R_3$,$R_4$, $R_5$, and $R_6$ groups are selected from hydrogen, methyl, ethyl, propyl, isopropyl, cyclopropyl, —F, —$CF_3$, —Cl, —Br, or —O—$CH_3$. A most preferred $R_3$, $R_4$, $R_5$, and $R_6$ is independently selected from hydrogen, C(O)$C_1$-$C_6$alkyl, C(O)O$C_1$-$C_6$alkyl, COOH, and sodium and potassium salts thereof.

A preferred compound of the invention is a compound selected from the group consisting of:
3-Oxo-3H-benzo[d]isothiazole-2-carboxylic acid allylamide;
3-Oxo-3H-benzo[d]isothiazole-2-carboxylic acid pentylamide;
3-Oxo-3H-benzo[d]isothiazole-2-carboxylic acid hexylamide;
3-Oxo-3H-benzo[d]isothiazole-2-carboxylic acid (5-methylhexyl)-amide;
3-Oxo-3H-benzo[d]isothiazole-2-carboxylic acid dodecylamide;
3-Oxo-3H-benzo[d]isothiazole-2-carboxylic acid cyclohexylamide;
3-Oxo-3H-benzo[d]isothiazole-2-carboxylic acid benzylamide;
3-Oxo-3H-benzo[d]isothiazole-2-carboxylic acid 2-methylbenzylamide;
3-Oxo-3H-benzo[d]isothiazole-2-carboxylic acid 3-methylbenzylamide;
3-Oxo-3H-benzo[d]isothiazole-2-carboxylic acid 4-methylbenzylamide;
3-Oxo-3H-benzo[d]isothiazole-2-carboxylic acid 2-ethyl-6-methyl-benzylamide;
3-Oxo-3H-benzo[d]isothiazole-2-carboxylic acid 2-isopropyl-6-methyl-benzylamide;
3-Oxo-3H-benzo[d]isothiazole-2-carboxylic acid phenethylamide;
3-Oxo-3H-benzo[d]isothiazole-2-carboxylic acid (2-thiophen-2-yl-ethyl)-amide;
3-Oxo-3H-benzo[d]isothiazole-2-carboxylic acid (3-phenylpropyl)-amide;
3-Oxo-3H-benzo[d]isothiazole-2-carboxylic acid (4-phenylbutyl)-amide;
3-Oxo-3H-benzo[d]isothiazole-2-carboxylic acid (4-cyclohexyl-butyl)-amide;
5-Methyl-3-oxo-3H-benzo[d]isothiazole-2-carboxylic acid butylamide;
6-Chloro-3-oxo-3H-benzo[d]isothiazole-2-carboxylic acid propylamide;
6-Chloro-3-oxo-3H-benzo[d]isothiazole-2-carboxylic acid isopropylamide;
6-Chloro-3-oxo-3H-benzo[d]isothiazole-2-carboxylic acid butylamide;
6-Chloro-3-oxo-3H-benzo[d]isothiazole-2-carboxylic acid hexylamide;
6-Chloro-3-oxo-3H-benzo[d]isothiazole-2-carboxylic acid cyclohexylamide;
6-Chloro-3-oxo-3H-benzo[d]isothiazole-2-carboxylic acid benzylamide, and pharmaceutically acceptable salts thereof.

More preferred compounds of the invention are represented by the formulae (C1), (C2), (C3), and (C4):

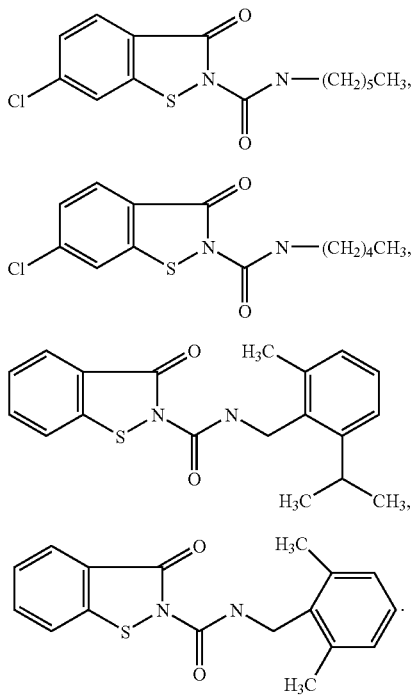

The salts of the benz(d)isothiazole-3(2H)-one compounds represented by formula (I), are an additional aspect of the invention.

In those instances when the compound of the invention possesses acidic or basic functional groups, various salts may be formed which are more water soluble and more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66:1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities and can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier. Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N, N-diethylacetamide (available from Aldrich Chemical Co., Milwaukee, Wis. USA; Item No. 25,099-6).

Morpholinylethyl ester prodrugs may be prepared by reaction of the sodium salt of a compound of formula (I) (in a medium such as dimethylformamide) with 4-(2-chloroethyl)morpholine hydrochloride (available from Aldrich Chemical Co., Milwaukee, Wis. USA, Item No. C4, 220-3).

Preparing the Compounds of the Invention

Compounds of the invention may be prepared according to the following scheme 1 and variations thereof known to one of skill in the art.

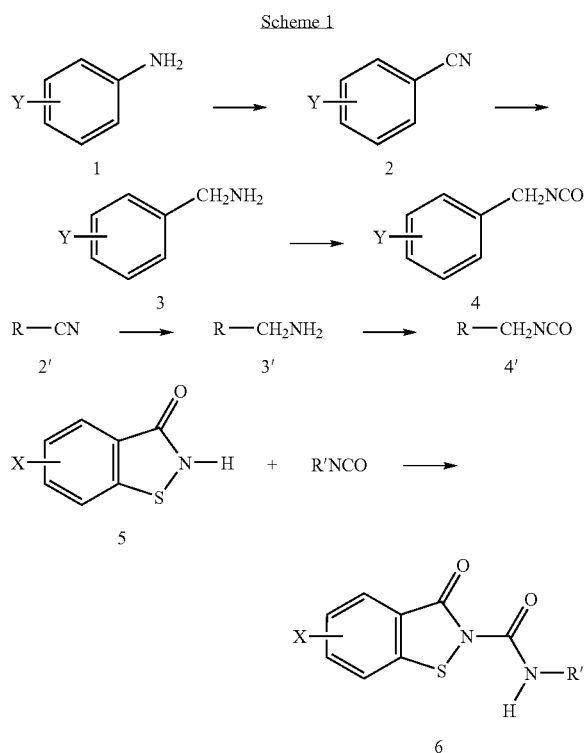

Scheme 1 depicts a protocol for preparing benzisothiazole-3(2H)-one-compounds of the invention starting from an aniline derivative 1 (available from Aldrich Chemical Co. Milwaukee U.S.A, and other fine chemical suppliers) or substituted analogs thereof. The starting material 1 is reacted with tert-butylnitrite to form a diazonium ion intermediate which further reacts with available cyanide ion (from copper cyanide) to afford the benzonitrile compound 2. The nitrile 2 or analog thereof, is reduced to afford the subsituted methylamine compound 3. The reduction of the nitrile to the amine may be accomplished using stannous chloride or other reducing agents following procedures known to one of skill in the art. The substituted methylamine compound 3 is converted to the isocyanate compound 4 in an aprotic solvent such as anhydrous methylene chloride. The convertion to the isocyanate is accomplished using phosgene (available from Aldrich Chemical Company, Milwaukee, USA and other fine chemical manufacturers) in the presence of a proton sponge i.e. triethylamine, to afford the isocyanate compound 4 or analog thereof. The isocyanate 4 or 4' is reacted with a solution of benz[d]isothiazol-3-one in a suitable solvent e.g., anhydrous methylene chloride at temperatures ranging from about 10° C. to 60° C. More generally, compounds of the invention are prepared by reacting a nitrile 2' purchased from commercial sources or prepared by methods known to one of skill in the art, with a reducing agent to form the primary methylamine compound 3'. The methylamine 3' is converted to the isocyanate by methods known to one of skill in the art. The isocyanate 4) or 4' is then reacted with benz[d]isothiazol-3-one 5 or substituted analogs thereof to afford the compound(s) of the invention, such as compound 6. Benz[d] isothiazole-3-one 5 also named 1,2-benzoisothiazolin-3-one is available from commercial suppliers, including for example, MDA Chemicals Limited, Willow Mill, Caton, Lancaster LA2 9RA, UK. Analogs of benz[d]isothiazole-3- one may be obtained by methods described in the examples and/or known to one of skill in the art.

Compounds of formula I wherein one or all of $R_3$, $R_4$, $R_5$, and $R_6$ are other than hydrogen are made starting with purchased starting materials having the requisite substitutents or with starting materials made by methods known to one of skill in the art. Examples of such known methods include the methods described in general reference texts such as Organic Functional Group Preparations, $2^{nd}$ Edition, 1989; Comprehensive Organic Transformations, VCH Publishers Inc, 1989; Compendium of Organic Synthetic Methods, Volumes 1-10, 1974-2002, Wiley Interscience; March's Advanced Organic Chemistry, Reactions Mechanisms, and Structure, $5^{th}$ Edition, Michael B. Smith and Jerry March, Wiley Interscience, 2001, Advanced Organic Chemistry, $4^{th}$ Edition, Part B, Reactions and Synthesis, Francis A. Carey and Richard J. Sundberg, Kluwer Academic/Plenum Publishers, 2000, etc., and references cited therein.

Methods of Using the Compounds of the Invention

The benzisothiazole-3(2H)-one compounds described herein are believed to achieve their beneficial therapeutic action principally by direct inhibition of hepatic lipase and/or endothelial lipase activity.

The method of the invention for inhibiting hepatic lipase and/or endothelial lipase activity with a therapeutically effective amount of a benzisothiazole-3(2H)-one compound of Formula (I) including a combination thereof, or a salt or a prodrug derivative thereof as described herein.

Another aspect of this invention relates to inhibition and/or prevention of "Hepatic Lipase-Mediated Diseases" such as hypercholesterolemia, hyperlipidemia, atherosclerosis and related diseases as described earlier. The method comprises administering to a mammal (including a human) in need of such treatment a therapeutically effective amount of a benzisothiazole-3(2H)-one compound of the invention.

As previously noted, the compounds of the invention are useful for inhibiting hepatic lipase and/or endothelial lipase activity. By the term, "inhibiting" is meant the prevention or therapeutically significant reduction in release of hepatic lipase and/or endothelial lipase by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or ameliorative or prophylactic effect will, of course, be determined by the particular circumstances surrounding the case, including, for example, the compound administered, the route of administration and the condition being treated. Typical daily doses will contain a non-toxic dosage level of from about 0.01 mg/kg to about 50. mg/kg of body weight of an active compound of this invention.

Preferably compounds of the invention per Formula (I) or pharmaceutical formulations containing these compounds are in unit dosage form for administration to a mammal. The unit dosage form can be a capsule or tablet itself, or the appropriate number of any of these. The quantity of Active Ingredient in a unit dose of composition may be varied or adjusted from about 0.1 to about 500 milligrams or more according to the particular treatment involved. It should be appreciated that it may be necessary to make routine variations to the dosage depending on the age and condition of the patient. The dosage will also depend on the route of administration.

The compound can be administered by a variety of routes including oral, aerosol, transdermal, sublingual, subcutaneous, intravenous, intramuscular, or intranasal.

Pharmaceutical formulations of the invention are prepared by combining (e.g., mixing) a therapeutically effective amount of the benzisothiazole-3(2H)-one compound of the invention together with a pharmaceutically acceptable carrier or diluent therefor. The present pharmaceutical formulations are prepared by known procedures using well-known and readily available ingredients.

In making the compositions of the present invention, the Active Ingredient will usually be admixed with a carrier, or diluted by a carrier, or enclosed within a carrier, which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substance, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. A preferred tablet formulation for oral administration is one that affords rapid dissolution in the mouth of a patient in need thereof.

In powders the carrier is a finely divided solid, which is in admixture with the finely divided Active Ingredient. In tablets the Active Ingredient is mixed with a carrier having the necessary binding properties in suitable proportions and compacted in the shape and size desired. The powders and tablets preferably contain from about 1 to about 99 weight percent of the Active Ingredient, which is the novel compound of this invention. Suitable solid carriers are magnesium carbonate, magnesium stearate, talc, sugar lactose, pectin, dextrin, starch, gelatin, tragacanth, methylcellulose, sodium carboxymethyl cellulose, low melting waxes, and cocoa butter.

Sterile liquid form formulations include suspensions, emulsions, syrups and elixirs.

The Active Ingredient can be dissolved or suspended in a pharmaceutically acceptable carrier, such as sterile water, sterile organic solvent or a mixture of both. The Active Ingredient can often be dissolved in a suitable organic solvent, for instance aqueous propylene glycol. Other compositions can be made by dispersing the finely divided Active Ingredient in aqueous starch or sodium carboxymethyl cellulose solution or in a suitable oil.

The following pharmaceutical formulations 1 through 8 are illustrative only and are not intended to limit the scope of the invention in any way. "Active Ingredient", refers to a compound according to Formula (I) or a pharmaceutically acceptable salt, solvate, racemate or enantiomer thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active Ingredient, are made as follows:

| Active Ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, arid filled into hard gelatin capsules in 200 mg quantities.

Formulation 6

Suppositories, each containing 225 mg of Active Ingredient, are made as follows:

| | |
|---|---|
| Active Ingredient | 225 mg |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active Ingredient | 100 mg |
| Isotonic saline | 1,000 ml |

The solution of the above ingredients generally is administered intravenously to a subject at a rate of 1 ml per minute.

The abbreviations, symbols and terms used in the examples have the following meanings.
Ac=acetyl
Anal.=elemental analysis
calcd=calculated
Cpd.=compound
DMF=dimethylformamide
DMSO=dimethylsulfoxide
Et=ethyl
EtOAc=ethyl acetate
EtOH=ethanol
EtSH=ethanethiol
ESIMS=Electrospray Ionization Mass Spectrometry
FAB=Fast Atom Bombardment (Mass Spectroscopy)
FDMS=field desorption mass spectrum
Hex=hexanes
HL=Hepatic Lipase
HPLC=High Performance Liquid Chromatograph
HRMS=high resolution mass spectrum
IR=Infrared Spectrum
Me=methyl
MeI=methyl iodide
MeOH=methanol
MPLC=Medium Pressure Liquid Chromatography
NMR=Nuclear Magnetic Resonance
PPA=polyphosphoric acid
Rochelle's Salt=potassium sodium tartrate
RPHPLC=Reversed Phase High Performance Liquid Chromatography
$SiO_2$=silica gel
SM=starting material
Temp.=temperature
TFA=trifluoroacetic acid
THF=tetrahydrofuran
TLC=thin layer chromatography Hepatic Lipase Phospholipase Assay Compounds of the present invention were found to be efficacious in-vitro in inhibiting the release of hepatic lipase and/or endothelial lipase. Efficacy was determined by testing various compounds of the invention in a hepatic lipase and/or endothelial lipase assay discussed below, and disclosed in U.S. patent application Ser. No. 09/609, 871 filed Jul. 3, 2000 incorporated herein in its entirety for U.S Patent Office purposes.

Reagents
Substrate Buffer A: 100 mM Hepes, pH 8.3 at 37° C.
Substrate Buffer B: 100 mM Hepes, pH 8.3 at 37° C. with 6.83 mM Triton X100
ThioPEG: Molecular wt. of 540
Recombinant Hepatic Lipase
Thiophospholipid: about 0.42 mM thiophospholipid in chloroform DTNB Solution: about 50 nM DTNB in DMSO (dimethyl sulfoxide)

Hepes Buffer A

For Hepes Buffer A, there is 2.4 g Hepes/100 mL water. Therefore 36 grams of Hepes is dissolved in 1500 mL of water. The mix solution's pH is adjusted to pH83 at 37° C. and brought up to 1500 mL with water. 500 mL of Buffer A is retained for the Protein Buffer.

Hepes Buffer B

To the remaining 1000 mL of Hepes Buffer A, 4.49 g of Triton X-100 is added and then the combination mixed on a stir plate. It is optimal that stock Buffer A not be too cold or Triton X-100 will take a long time to go into solution ThioPEG Substrate Solution For 0.42 mM substrate stock, use 0.227 mg of thioPEG/mL of Substrate Buffer B. Approximately 20 mg of sn-1 thiol substituted Phosphatidyl Ethylene Glycol (see Examples for preparation method) is weighed into a vial, such as a scintillation vial. Enough chloroform should be added to make a 2.043 mg/mL solution. Sonicate the solution briefly until well dissolved. Next, pipette 1 mL of chloroform/substrate solution into each scintillation vial. This should give enough substrate for one full 96 well plate. Each vial is dried with nitrogen until solvent removed, swirling each vial simultaneously such that a thin film of substrate will be easily reconstituted in each buffer. Each vial is then frozen.

Daily stock preparation is-performed for 9 mL of substrate (one microtiter plate). On the day of the assay, the substrate vial is removed from the freezer and combined with 9 mL of pre-warmed (37° C.) substrate buffer (the final concentration is 0.227 mg/mL). Place the buffer in a 37° C. water bath. Sonicate for 5 minutes or vortex until solution is clear before use.

Enzyme Solution

The enzyme is stored at −80° C. in 100 or 50 μL portions. A 0.406 mg/mL recombinant hepatic lipase and/or endothelial lipase stock requires a 50-fold dilution. Therefore, to a 50 μl or 100 μl enzyme aliquot, 2450 μl or 4900 μl, respectively, of substrate Buffer A (protein buffer) should be added. The enzyme should then be stored on ice until ready to use. The protein concentration of enzyme is about 0.406 mg/mL.

DTNB Solution

To make a 20 mg/mL stock solution, 2-3 mg of DTNB is weighed and then mixed with an appropriate amount of 100% DMSO (dimethyl sulfoxide) to make the desired concentration. This mixture is sonicated for five minutes.

The above solution should be diluted 10 fold with substrate Buffer B (concentration now 2 mg/mL). Then to the thioPEG substrate solution, add 60 μl of dilute DTNB per mL of thioPEG substrate solution. Thus for 9 mL of substrate, 540 microliters of dilute DTNB (final concentration in substrate solution=0.11 mg/mL).

Table 1 below shows final assay volumes and concentrations of various components used following the above procedure.

TABLE 1

Final Assay Volumes and Concentrations
Hepatic Lipase Phospholipase Assay

| Component | Assay Volume | Final Concentration |
|---|---|---|
| HL | 10 μl | 12.5 nM |
| Test Cpd. | 10 μl | Varies |

TABLE 1-continued

Final Assay Volumes and Concentrations
Hepatic Lipase Phospholipase Assay

| Component | Assay Volume | Final Concentration |
|---|---|---|
| ThioPEG Substrate | 80 μl | 90 mM Hepes |
| (stock = 0.42 mM + | | 5.8 mM TX100 |
| substrate buffer) | | 0.336 mM ThioPEG |
| | | (0.06 mol fraction) |
| | | 0.088 mM DTNB/mL |

Sample Preparation

The test compound is dissolved in pure DMSO at 1 μM (1000 nM). As shown below in Table 2, assay concentrations are 10, 1, 0.1, 0.33, 0.011, 0.0037, 0.0012 and 0.00041 μM. Table 2 shows the assay concentrations and the corresponding volume of stock and 10% DMSO for each concentration.

TABLE 2

Assay concentrations for compound preparation

| Concentration (μM) | Assay Conc. (μM) | Microliters of stock solution | Diluents |
|---|---|---|---|
| 100 | 10 | 50 of 1 mM in straight DMSO | 450 μl of WATER |
| 10 | 1 | 5 μl of 100 μM | 450 μl 10% DMSO |
| 1 | 0.1 | 50 μl of 10 μM | 450 μl 10% DMSO |
| 0.33 | 0.033 | 200 μl of 1 μM | 400 μl 10% DMSO |
| 0.11 | 0.011 | 200 μl of 0.33 μM | 400 μl 10% DMSO |
| 0.037 | 0.0037 | 200 μl of 0.11 μM | 400 μl of 10% DMSO |
| 0.012 | 0.0012 | 200 μl of 0.037 μM | 400 μl of 10% DMSO |
| 0.0041 | 0.00041 | 200 μl of 0.012 μM | 400 μl of 10% DMSO |

Assay Procedure

Using a spectrometer, DTNB is used as a thiol coloring reagent with an incubator temperature of 37° C. Substrate Buffer B is placed in a 37° C. water bath to pre-warm. The substrate is removed from the freezer and 9 mL of substrate Buffer B, 100 mM Hepes, 6.83 mM Tx-100) is added, sonicated for 5 min. and then kept in a 37° C. water bath. Dilutions of the test compound are next made in preparation for assay.

10 μl of the diluted test compound are transferred via pipette into the wells. Control wells receive 10 μl each of 10% DMSO and enzyme solution, while blank wells receive 10 microliters of 10% DMSO and 10 microliters of saline (no enzyme).

Next, DTNB is weighed and diluted to 20 mg/mL with DMSO. The DTNB is then diluted 10 fold with the substrate Buffer B. 540 μl of diluted DTNB is added to 9 ml of Thio-PEG and mixed well.

The stock enzyme is diluted with Buffer A. Next, 10 microliters of protein solution is added to each well except the blank, and the wells mixed. The stock solution and test compounds are incubated at 37° C. for 10 min. At 10 minutes, 80 microliters of substrate are added to each well. The plate is then placed in the spectrometer and read at 412 nM every 2 minutes for 30 minutes.
Hepatic Lipase Assay Results
| Compounds | IC$_{50}$ (nM) |
|---|---|
| 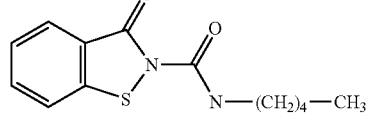 | 879 ± 24 |
| 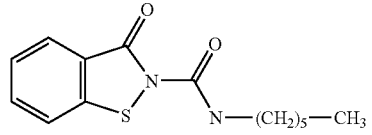 | 724 ± 16 |
| 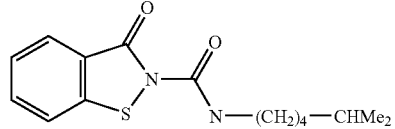 | 622 ± 19 |
| 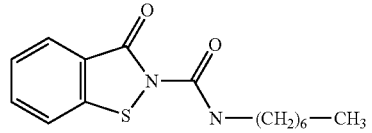 | 757 ± 18 |
| 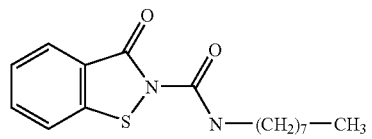 | 649 ± 17 |
| 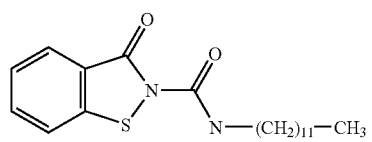 | 933 ± 34 |
| 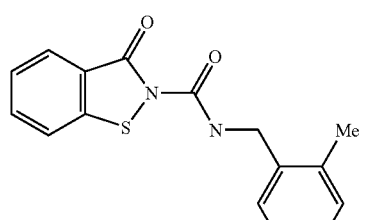 | 183 ± 6 |
| 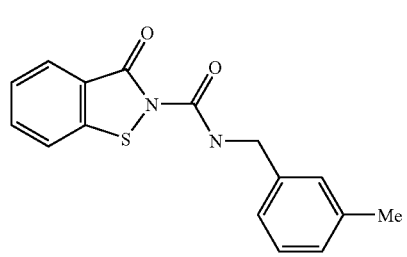 | 409 ± 14 |
-continued
| Compounds | IC$_{50}$ (nM) |
|---|---|
| 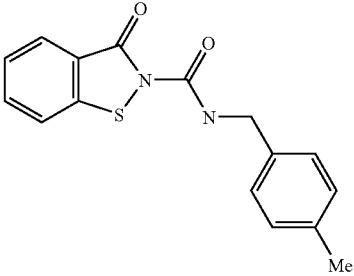 | 671 ± 18 |
| 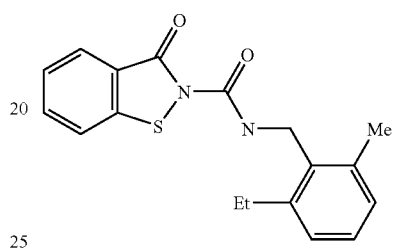 | 237 ± 4 |
| 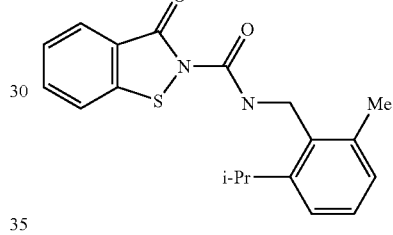 | 238 ± 13 |
| 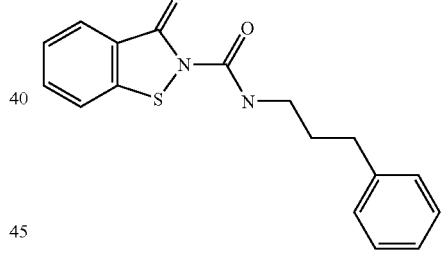 | 430 ± 19 |
| 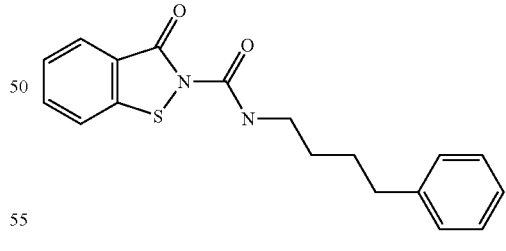 | 458 ± 16 |
| 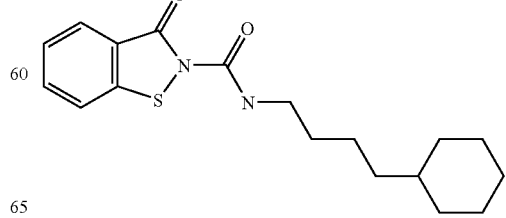 | 482 ± 21 |

-continued

| Compounds | IC$_{50}$ (nM) |
|---|---|
| [6-chloro-benzo[d]isothiazol-3-one with N-C(O)-NH-isopropyl] | 626 ± 20 |
| [6-chloro-benzo[d]isothiazol-3-one with N-C(O)-NH-(CH$_2$)$_4$-CH$_3$] | 532 ± 10 |
| [6-chloro-benzo[d]isothiazol-3-one with N-C(O)-NH-(CH$_2$)$_5$-CH$_3$] | 333 ± 8 |
| [6-chloro-benzo[d]isothiazol-3-one with N-C(O)-NH-cyclohexyl] | 419 ± 7 |
| [6-chloro-benzo[d]isothiazol-3-one with N-C(O)-NH-CH$_2$-phenyl] | 893 ± 48 |

Characterization of endothelial lipase activity

Hepatic lipase (HL) and endothelial lipase (EL) were expressed from AV12 cells. Aliquots from one days collection of media were stored at −70° C. Activity was measured for both enzymes in conditioned media, (non-purified) where they were tested on the same plate with Thio PEG substrate (0.06 mol fraction, 7.24 mM total lipid), at 37° C. for 30 minutes. The HL, at 1×, had an OD of 14.7. The OD for EL at 1× was 6.029. Therefore, when HL was used in studies where it was compared to EL, the HL was at 0.25× and EL was used at 1×. All experiments were done in triplicate with enzyme from conditioned media.

Kinetic experiments for EL were done varying the total lipid with a constant 0.044 mol fraction determining that a 10 mM total lipid was optimal. In addition, kinetic experiments varying the mol fractions with a constant total lipid showed that 0.03 mol fraction was optimal. Each experiment was run three times.

Experiments to determine proper pH of the substrate to be used with EL were performed at 37° C. with the above-mentioned conditions. The enzyme was tested at pH 7.0, 7.4 and 8.3. The order of addition of reagents/enzyme was as follows: 10 μL of 10% DMSO, 80 μL of substrate and 10 μL of enzyme. Data represents an average of three experiments.

Temperature of the assay was varied from 26.9° C. to 37° C. with the above-mentioned conditions. This was the temperature of the incubation during the 30-minute read. The pH of the substrate was 8.3. The order of addition of reagents/enzyme was as follows: 10 μL of 10% DMSO, 80 μL of substrate and 10 μL of enzyme. Each experiment was run three times. Data is an average of these experiments.

Substrate specificity was determined by testing the activity of HL and EL with Thio Phosphatidylethylene glycol (PEG) and Thio-phosphatidylethanolamine (PE).

Assay conditions of assay were as follows. Both substrates for EL were run at 0.03 mol fraction, 10 mM total lipid. They were dissolved in 100 mM Hepes with 9.95 mM TX100. Both substrates for HL were run at 0.06 mol fraction and 7.25 mM total lipid. They were dissolved in 100 mM Hepes with 6.83mM Triton X100. The EL enzyme was used at 1× and the HL enzyme was used at 0.25×. The order of addition was as follows: 10 μL of 10% DMSO, 80 μL of substrate and 10 μL of enzyme. The DMSO and substrate were incubated for 10 minutes at 37° C. before the addition of the enzyme. DTNB was added to the substrate prior to addition to the well at 0.096 mg/mL final plate concentration. The experiments were performed 3 times. Data represents an average of these.

While the present invention has been illustrated above by certain specific embodiments, it is not intended that these specific examples should limit the scope of the invention as described in the appended claims.

Experimental

All of the products of the Examples described below as well as intermediates used in the following procedures showed satisfactory NMR and IR spectra. They also had the correct mass spectral values.

EXAMPLE 1

The preparation of
3-Oxo-3H-benzo[d]isothiazole-2-carboxylic acid ethylamide

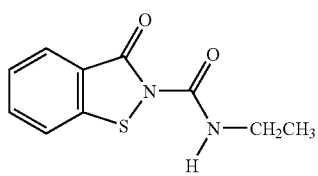

6a

Ethyl isocyanate (68.0 μL, 0.838 mmol) was added to a stirred solution of benzo[d]isothiazol-3-one (106 mg, 0.698 mmol) in anhydrous THF (2 mL) at ambient temperature under nitrogen. The resultant mixture was heated in an oil bath at 45° C. for 1 hr. After concentration and subsequent flash chromatography on silica (CH$_2$Cl$_2$), compound 6a was obtained as a white solid (71.1 mg, 46% yield). mp 123-124° C.; IR(CHCl$_3$) 3290, 1710, 1662, 1542 cm$^{-1}$; $^1$H-NMR (CDCl$_3$) δ1.22-1.54 (m, 3H), 3.44-3.53 (m, 2H), 7.42 (t, J=7.5 Hz, 1H), 7.58 (d, J=7.5 Hz, 1H), 7.69 (t, J=7.5 Hz, 1H), 8.01 (d, J=7.5 Hz, 1H), 8.84 (br s, 1H); ESIMS m/e 223 (M$^+$+1).

Elemental Analyses for $C_{10}H_{10}N_2O_2S \cdot 0.3H_2O$: Calculated: C, 52.75; H, 4.69; N, 12.30 Found: C, 52.91; H, 4.44; N, 11.97

EXAMPLE 2

The preparation of 3-Oxo-3H-benzo[d]isothiazole-2-carboxylic acid propylamide

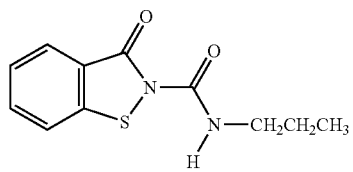

6b

Following the synthetic procedure of 6a as described in Example 1, compound 6b (77% yield) was synthesized from benzo[d]isothiazol-3-one and n-propyl isocyanate as a white solid. mp 90-91° C.; IR(CHCl$_3$) 3290, 1712, 1662, 1542 cm$^{-1}$; $^1$H-NMR (CDCl$_3$) δ1.00 (t, J=7.3 Hz, 3H), 1.52-1.72 (m, 2H), 3.39-3.44 (m, 2H), 7.42 (t, J=7.8 Hz, 1H), 7.57 (d, J=7.8 Hz, 1H), 7.70 (t, J=7.8 Hz, 1H), 8.01 (d, J=7.8 Hz, 1H), 8.89 (br s, 1H); ESIMS m/e 237 (M$^+$+1).

Elemental Analyses for $C_{11}H_{12}N_2O_2S$: Calculated: C, 55.91; H, 5.12; N, 11.86 Found: C, 55.66; H, 5.07; N, 11.70

EXAMPLE 3

The preparation of 3-Oxo-3H-benzo[d]isothiazole-2-carboxylic acid allylamide

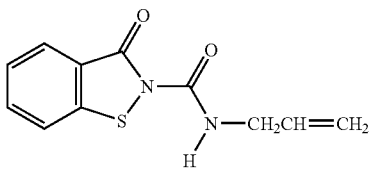

6c

Following the synthetic procedure of 6a as described in Example 1, compound 6c (67% yield) was synthesized from benzo[d]isothiazol-3-one and allyl isocyanate as a white solid. mp 116-119° C.; IR(CHCl$_3$) 3290, 1711, 1664, 1537 cm$^{-1}$; $^1$H-NMR (CDCl$_3$) δ 4.05-4.10 (m, 2H), 5.18-5.34 (m, 2H), 5.83-5.99 (m, 1H), 7.43 (t, J=7.2 Hz, 1H), 7.58 (d, J=7.2 Hz, 1H), 7.70 (t, J=7.2 Hz, 1H), 8.02 (d, J=7.2 Hz, 1H), 8.99 (br s, 1H); ESIMS m/e 235 (M$^+$+1).

Elemental Analyses for $C_{11}H_{10}N_2O_2S$: Calculated: C, 56.40; H, 4.30; N, 11.96 Found: C, 56.29; H, 4.39; N, 12.25

EXAMPLE 4

The preparation of 3-Oxo-3H-benzo[d]isothiazole-2-carboxylic acid pentylamide

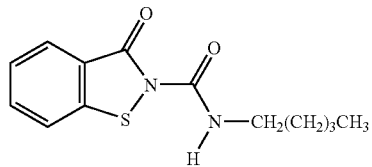

6d

Following the synthetic procedure-of 6a as described in Example 1, compound 6d (80% yield) was synthesized from benzo[d]isothiazol-3-one and n-butyl isocyanate as a white solid. mp 42-44° C.; IR(CHCl$_3$) 3290, 1711, 1662, 1540 cm$^{-1}$; $^1$H-NMR (CDCl$_3$) δ0.83-0.87 (m, 3H), 1.25-1.34 (m, 4H), 1.54-1.60 (m, 2H), 3.35-3.40 (m, 2H), 7.36 (t, J=7.8 Hz, 1H), 7.51 (d, J=7.8 Hz, 1H), 7.63 (t, J=7.8 Hz, 1H), 7.95 (d, J=9.2 Hz, 1H), 8.81 (br s, 1H); ESIMS m/e 265 (M$^+$+1).

Elemental Analyses for $C_{13}H_{16}N_2O_2S \cdot 0.2H_2O$: Calculated: C, 58.27; H, 6.17; N, 10.45 Found: C, 58.21; H, 6.24; N, 10.44

EXAMPLE 5

The preparation of 3-Oxo-3H-benzo[d]isothiazole-2-carboxylic acid hexylamide

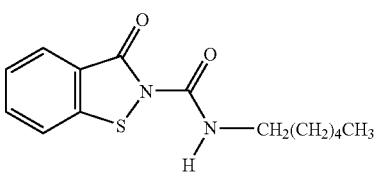

6e

Following the synthetic procedure of 6a as described in Example 1, compound 6e (82% yield) was synthesized from benzo[d]isothiazol-3-one and n-hexyl isocyanate as a white solid. mp 52-53° C.; IR(CHCl$_3$) 3290, 1711, 1662, 1540 cm$^{-1}$; $^1$H-NMR (CDCl$_3$) δ0.80-0.87 (m, 3H), 1.21-1.35 (m, 6H), 1.53-1.61 (m, 2H), 3.34-3.40 (m, 2H), 7.36 (t, J=7.6 Hz, 1H), 7.51 (d, J=7.6 Hz, 1H), 7.63 (t, J=7.6 Hz, 1H), 7.95 (d, J=6.9 Hz, 1H), 8.81 (br s, 1H); ESIMS m/e 279 (M⁺+1).

EXAMPLE 6

The preparation of 3-Oxo-3H-benzo[d]isothiazole-2-carboxylic acid (5-methyl-hexyl)-amide

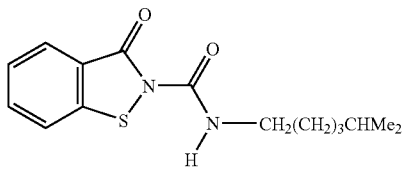

6f

A. The preparation of(1-Isocyanato-5-methyl)-hexane

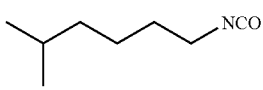

4a'

A solution of 5-(methyl)hexylamine (407 mg, 3.53 mmol) and proton sponge (1.51 g, 7.06 mmol) in anhydrous CH₂Cl₂ (6 mL) was added dropwise to a stirred solution of triphosgene (419 mg, 1.41 mmol) in anhydrous CH₂Cl₂ (6 mL) at 0° C. The resultant solution was allowed to stir at ambient temperature for 15 minutes. After dilution with CH₂Cl₂ (40 mL), the mixture was washed with 1N HCl (15×2 mL) and water (15 mL). The organic layer was dried over Na₂SO₄, filtered and concentrated to give the desired isocyanate 4a' (365 mg, 73% yield) as an oil. ¹H-NMR (CDCl₃) δ0.88 (d, J=6.6 Hz, 6H), 1.16-1.23 (m, 2H), 1.32-1.42 (m, 2H), 1.50-1.62 (m, 3H), 3.29 (t, J=6.6 Hz, 2H).

B. The preparation of 3-Oxo-3H-benzo[d]isothiazole-2-carboxylic acid (5-methyl-hexyl)-amide

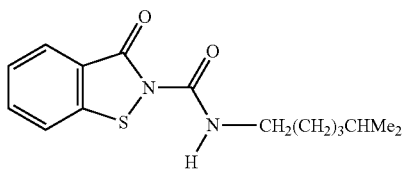

6f

Following the synthetic procedure of 6a as described in Example 1, compound 6f was synthesized from benzo[d]isothiazol-3-one and isocyanate 4a' as a white solid. mp 49-51° C.; IR(CHCl₃) 3289, 1711, 1662, 1538 cm⁻¹; ¹H-NMR (DMSO-d₆) δ0.84 (d, J=6.6 Hz, 6H), 1.13-1.20 (m, 2H), 1.26-1.32 (m, 2H), 1.47-1.55 (m, 3H), 3.28-3.34 (m, 2H), 7.47 (t, J=7.9 Hz, 1H), 7.78 (t, J=7.9 Hz, 1H), 7.93 (d, J=7.9 Hz, 1H), 8.00 (d, J=7.9 Hz, 1H), 8.84 (br t, J=5.5 Hz, 1H); ESIMS m/e 293 (M⁺+1).

Elemental Analyses for C₁₅H₂₀N₂O₂S: Calculated: C, 61.62; H, 6.89; N, 9.58 Found: C, 61.32; H, 6.90; N, 9.41

EXAMPLE 7

The preparation of 3-Oxo-3H-benzo[d]isothiazole-2-carboxylic acid dodecylamide

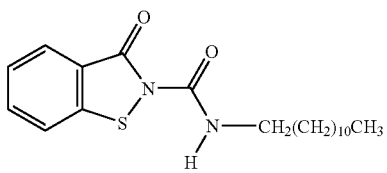

6g

Following the synthetic procedure of 6a as described in Example 1, compound 6g (78% yield) was synthesized from benzo[d]isothiazol-3-one and dodecyl isocyanate as a white solid. mp 66-67° C.; IR(CHCl₃) 3279, 1709, 1660, 1536 cm⁻¹; ¹H-NMR (CDCl₃) δ0.87 (t, J=6.8 Hz, 3H), 1.20-1.39 (m, 18H), 1.59-1.66 (m, 2H), 3.40-3.46 (m, 2H), 7.42 (t, J=7.6 Hz, 1H), 7.57 (d, J=7.6 Hz, 1H), 7.69 (t, J=7.6 Hz, 1H), 8.01 (d, J=7.6 Hz, 1H), 8.87 (br s, 1H); ESIMS m/e 363 (M⁺+1).

EXAMPLE 8

The preparation of 3-Oxo-3H-benzo[d]isothiazole-2-carboxylic acid cyclohexylamide

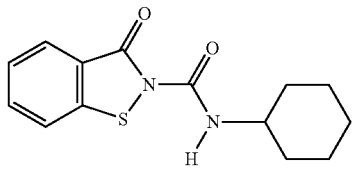

6h

Following the synthetic procedure of 6a as described in Example 1, compound 6h (52% yield) was synthesized from benzo[d]isothiazol-3-one and cyclohexyl isocyanate as a white solid. mp 49-51° C; IR(CHCl₃) 3287, 1711, 1660, 1533 cm⁻¹; ¹H-NMR (CDCl₃) δ 1.20-1.65 (m, 6H), 1.65-1.80 (m, 2H), 1.95-2.05 (m, 2H), 3.80-3.94 (m, 1H), 7.42 (t, J=7.6 Hz, 1H), 7.58 (d, J=7.6 Hz, 1H), 7.69 (t, J=7.6 Hz, 1H), 8.00 (d, J=7.6 Hz, 1H, 8.86 (br s, 1H); ESIMS m/e 277 (M⁺+1).

EXAMPLE 9

The preparation of 3-Oxo-3H-benzo[d]isothiazole-2-carboxylic acid benzylamide

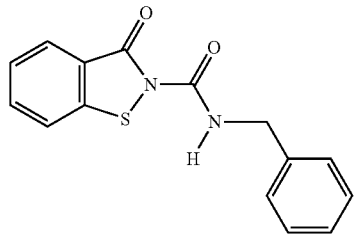

6i

Following the synthetic procedure of 6a as described in Example 1, compound 6i (88% yield) was synthesized from benzo[d]isothiazol-3-one and benzyl isocyanate as a white solid. mp 169-170° C.; IR(CHCl$_3$) 3281, 1711, 1663, 1536 cm$^{-1}$; $^1$H-NMR (CDCl$_3$) δ4.64 (d, J=5.9 Hz, 2H), 7.28-7.45 (m, 5H), 7.58 (d, J=7.2 Hz, 1H), 7.70 (t, J=7.2 Hz, 1H), 8.01 (d, J=7.2 Hz, 1H), 9.26 (br s, 1H); ESIMS m/e 285 (M$^+$+1).

Elemental Analyses for C$_{15}$H$_{12}$N$_2$O$_2$S: Calculated: C, 63.36; H, 4.25; N, 9.85 Found: C, 63.35; H. 4.27; N, 9.84

EXAMPLE 10

The preparation of 3-Oxo-3H-benzo[d]isothiazole-2-carboxylic acid 2-methyl-benzylamide

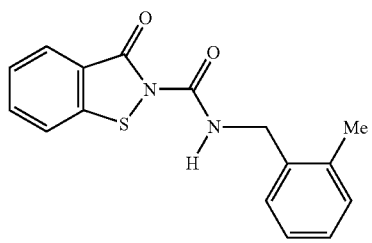

6j

Following the synthetic procedure of 6a as described in Example 1, compound 6j (56% yield) was synthesized from benzo[d]isothiazol-3-one and 2-methylbenzyl isocyanate as a white solid. mp 184-186° C.; IR(CHCl$_3$) 3281, 1705, 1652, 1528 cm$^{-1}$; $^1$H-NMR (DMSO-d$_6$) δ2.32 (s, 3H), 4.52 (d, J=5.9 Hz, 2H), 7.15-7.19 (m, 3H), 7.27-7.30 (m, 1H), 7.48 (t, J=7.6 Hz, 1H), 7.78 (t, J=8.2 Hz, 1H), 7.93 (d, J=8.2 Hz, 1H), 8.01 (d, J=8.2 Hz, 1H), 9.18 (t, J=5.9 Hz, 1H); ESIMS m/e 299 (M$^+$+1).

Elemental Analyses for C$_{14}$H$_{16}$N$_2$O$_2$S: Calculated: C, 60.85; H, 5.84; N, 10.14 Found: C, 60.88; H, 5.73; N, 10.15

EXAMPLE 11

The preparation of 3-Oxo-3H-benzo[d]isothiazole-2-carboxylic acid 3-methyl-benzylamide

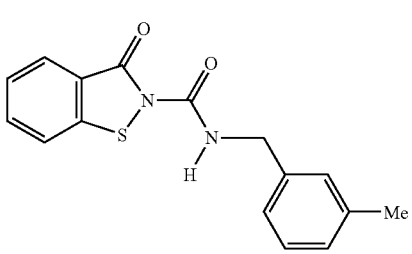

6k

Following the synthetic procedure of 6a as described in Example 1, compound 6k (37% yield) was synthesized from benzo[d]isothiazol-3-one and 3-methylbenzyl isocyanate as a white solid. mp 153-155° C.; IR(CHCl$_3$) 3281, 1711, 1650, 1534 cm$^{-1}$; $^1$H-NMR (DMSO-d$_6$) δ2.28 (s, 3H), 4.49 (d, J=5.9 Hz, 2H), 7.07 (d, J=7.5 Hz, 1H), 7.12-7.16 (m, 2H), 7.22 (t, J=7.5 Hz, 1H), 7.48 (t, J=7.8 Hz, 1H), 7.78 (t, J=8.2 Hz, 1H), 7.93 (d, J=7.8 Hz, 1H), 8.01 (d, J=8.2 Hz, 1H), 9.25 (br t, J=5.9 Hz, 1H); ESIMS m/e 299 (M$^+$+1).

Elemental Analyses for C$_{16}$H$_{14}$N$_2$O$_2$S: Calculated: C, 64.41; H, 4.73; N, 9.39 Found: C, 64.17; H, 4.60; N, 9.31

EXAMPLE 12

The preparation of 3-Oxo-3H-benzo[d]isothiazole-2-carboxylic acid 4-methyl-benzylamide

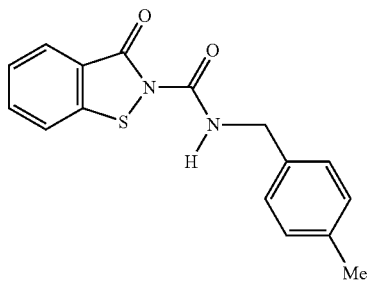

6l

Following the synthetic procedure of 6a as described in Example 1, compound 6l (54% yield) was synthesized from benzo[d]isothiazol-3-one and 4-methylbenzyl isocyanate as a white solid. mp 171-173° C.; IR(KBr) 3281, 1711, 1650, 1538 cm$^{-1}$; $^1$H-NMR (DMSO-d$_6$) δ2.27 (s, 3H), 4.48 (d, J=5.8 Hz, 2H), 7.14 (d, J=8.2 Hz, 2H), 7.24 (d, J=8.2 Hz, 2H), 7.48 (t, J=7.8 Hz, 1H), 7.78 (t, J=8.2 Hz, 1H), 7.93 (d, J=7.8 Hz, 1H), 8.01 (d, J=8.2 Hz, 1H), 9.22 (br t, J=5.8 Hz, 1H); ESIMS m/e 299 (M$^+$+1).

Elemental Analyses for $C_{16}H_{14}N_2O_2S$: Calculated: C, 64.41; H, 4.73; N, 9.39 Found: C, 64.20; H, 4.57; N, 9.30

EXAMPLE 13

The preparation of
3-Oxo-3H-benzo[d]isothiazole-2-carboxylic acid 2-ethyl-6-methyl-benzylamide

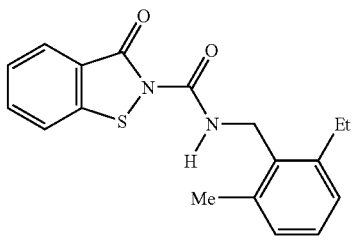

6m

A. The preparation of 2-Ethyl-6-methyl-benzylamine

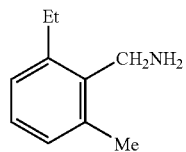

3a

Lithium aluminum hydride (20.5 mL, 1M in THF) was added dropwise to a stirred solution of 2-ethyl-6-methylbenzonitrile (2.38 g, 16.4 mmol) in anhydrous THF (20 mL) at ambient temperature under nitrogen. The resultant suspension was stirred for 16 hr. The reaction mixture was treated dropwise with methanol (5 mL), followed by the addition of saturated aqueous Rochelle's salt (60 mL), ethyl ether (60 mL) and water (20 mL). The two-layered mixture was stirred vigorously under nitrogen for 1 hr. The organic layer was separated, dried over $MgSO_4$ and concentrated to give 3a as an oil (2.40 g, 98%). $^1$H-NMR (CDCl$_3$) δ1.17 (t, J=7.4 Hz, 3H), 1.90 (br s, 2H), 2.34 (s, 3H), 2.66 (q, J=7.4 Hz, 2H), 3.82 (s, 2H), 6.95-7.07 (m, 3H); ESIMS m/e 150 (M$^+$+1).

B. The preparation of 1-Ethyl-2-isocyanatomethyl-3-methyl-benzene

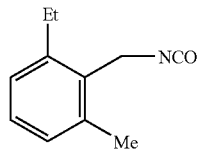

4a

A solution of 3a (307 mg, 2.06 mmol) and proton sponge (883 mg, 4.12 mmol) in anhydrous $CH_2Cl_2$ (5 mL) was added dropwise to a stirred solution of triphosgene (244 mg, 0.823 mmol) in anhydrous $CH_2Cl_2$ (5 mL) at 0° C. The resultant solution was allowed to stir at ambient temperature for 15 minutes. After dilution with $CH_2Cl_2$ (20 mL), the mixture was washed with 1N HCl (10 ×2 mL). The organic layer was dried over $Na_2SO_4$, filtered and concentrated to give the desired isocyanate 4a (332 mg, 92% yield) as an oil. $^1$H-NMR (CDCl$_3$) δ1.26 (t, J=7.5 Hz, 3H), 2.43 (s, 3H), 2.74 (q, J=7.5 Hz, 2H), 4.46 (s, 2H), 7.05-7.13 (m, 2H), 7.20 (t, J=7.5 Hz, 1 H).

C. The preparation of
3-Oxo-3H-benzo[d]isothiazole-2-carboxylic acid 2-ethyl-6-methyl-benzylamide

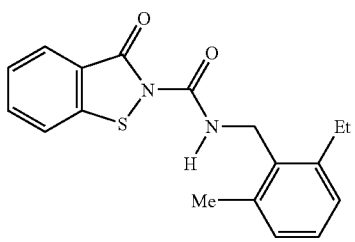

6m

Isocyanate 4a (332 mg, 1.89 mmol) was added to a stirred solution of benzo[d]isothiazol-3-one (286 mg, 1.89 mmol) in anhydrous THF (5 mL) at ambient temperature under nitrogen. The resultant mixture was heated in an oil bath at 45° C. for 4 hr. After concentration and subsequent flash chromatography on silica ($CH_2Cl_2$), compound 6m was obtained as a white solid (430 mg, 70% yield). mp 102-104° C.; IR(CHCl$_3$) 3281, 1709, 1663, 1525 cm$^{-1}$; $^1$H-NMR (DMSO-d$_6$) δ1.16 (t, J=7.6 Hz, 3H), 2.38 (s, 3H), 2.73 (t, J=7.6 Hz, 2H), 4.57 (d, J=5.5 Hz, 2H), 7.05-7.10 (m, 2H), 7.16 (t, J=7.8 Hz, 1H), 7.46 (t, J=8.1 Hz, 1H), 7.77 (t, J=7.8 Hz, 1H), 7.88 (d, J=8.1 Hz, 1H), 8.01 (d, J=8.1 Hz, 1H), 8.92 (br t, J=5.5 Hz, 1H); ESIMS m/e 327 (M$^+$+1).

Elemental Analyses for $C_{18}H_{18}N_2O_2S \cdot 0.1H_2O$: Calculated: C, 65.87; H, 5.59; N, 8.54 Found: C, 65.75; H, 5.42; N, 8.48

EXAMPLE 14

The preparation of
3-Oxo-3H-benzo[d]isothiazole-2-carboxylic acid 2-isopropyl-6-methyl-benzylamide

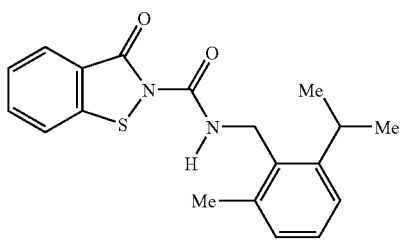

6n

A. The preparation of 2-isopropyl-6-methyl-benzonitrile

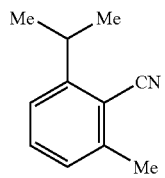

2b

CuCN (7.80 g, 87.2 mmol) was added to a stirred anhydrous DMSO (70 mL) at 60° C. to form a clear solution, then followed by the addition of tert-butyl nitrite (24.0 mL, 202 mmol) all at once. A solution of 2-isopropyl-6-menthylaniline (10.0 g, 67.0 mmol) in anhydrous DMSO (30 mL) was added dropwise, via an addition funnel, to the mixture. After the addition was complete, the reaction mixture was allowed to stir for 1 hr. After being cooled to 45° C., the mixture was slowly treated with 5N HCl (100 mL). Five minutes later, the reaction mixture was cooled to ambient temperature before it was extracted with EtOAc/hexane (1:1; 500×2 mL). The combined organic layers were washed with water (100 mL) and brine (100 mL), dried, concentrated in vacuo, then chromatographed on silica (0-5% EtOAc in hexane) to give 8.43 g of the crude nitrile 2b. IR(CHCl$_3$) 2220 cm$^{-1}$; $^1$H-NMR (CDCl$_3$) δ1.30 (d, J=6.9 Hz, 6H), 2.54 (s, 3H), 3.38 (h, J=6.9 Hz, 1H), 7.13 (d, J=7.8 Hz, 1H), 7.20. (d, J=7.8 Hz, 1H), 7.41 (t, J=7.8 Hz, 1H); ESIMS m/e 160 (M$^+$+1).

B. The preparation of 2-isopropyl-6-methyl-benzylamine

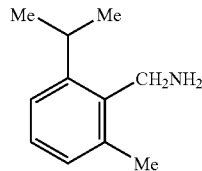

3b

To the crude ice-cold nitrile 2b (7.74 g, 48.6 mmol) in anhydrous Et$_2$O (70 mL) was slowly added lithium aluminum hydride (1N in Et$_2$O, 97.2 mL) under nitrogen. The resultant mixture was allowed to stir at ambient temperature for 16 hr. Then the reaction mixture was cooled at 0° C. and quenched with MeOH until the gas evolution stopped. EtOAc (500 mL) and saturated aqueous Rochelle's salt were added and the two-layered mixture was stirred vigorously under nitrogen for 1 hr to give two relatively clear layers. The organic layer was separated, dried over MgSO$_4$, filtered and concentrated, the crude oil was chromatographed on silica [20% EtOAc in hexane, then 1-2% (4.2 M Me$_3$N in EtOH) in CHCl$_3$]. Amine 3b (3.78 g, yield 48%) was obtained as a brown oil. IR(CHCl$_3$) 3300(br) cm$^{-1}$; $^1$H-NMR (CDCl$_3$) δ1.16 (d, J=6.8 Hz, 6H), 1.55 (br s, 2H), 2.33 (s, 3H), 3.28 (h, J=6.8 Hz, 1H), 3.71 (s, 2H), 6.92-6.95 (m, 1H), 7.03-7.10 (m, 2H); ESIMS m/e 164 (M$^+$+1).

C. The preparation of 2-Isocyanatomethyl-1-isopropyl-3-methyl-benzene

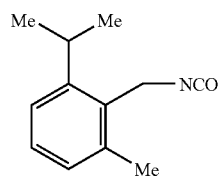

4b

A solution of 3b (956 mg, 5.85 mmol) and proton sponge (2.51 g, 11.7 mmol) in anhydrous CH$_2$Cl$_2$ (15 mL) was added dropwise to a stirred solution of triphosgene (695 mg, 2.34 mmol) in anhydrous CH$_2$Cl$_2$ (15 mL) at 0° C. The resultant solution was allowed to stir at ambient temperature for 15 minutes. After dilution with CH$_2$Cl$_2$ (30 mL), the mixture was washed with 1N HCl (15×2 mL) and water (20 mL). The organic layer was dried over Na$_2$SO$_4$, filtered and concentrated to give the desired isocyanate 4b (1.03 g, 93% yield) as an oil. $^1$H-NMR (CDCl$_3$) δ1.27 (t, J=6.8 Hz, 6H), 2.42 (s, 3H), 3.23 (h, J=6.8 Hz, 1H), 4.48 (s, 2H), 7.04-7.07 (m, 1H), 7.18-7.26 (m, 2H).

D. The preparation of 3-Oxo-3H-benzo[d]isothiazole-2-carboxylic acid 2-isopropyl-6-methyl-benzylamide

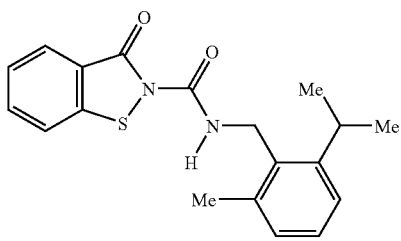

6n

Isocyanate 4b (273 mg, 1.44 mmol) was added to a stirred solution of benzo[d]isothiazol-3-one (218 mg, 1.44 mmol) in anhydrous THF (5 mL) at ambient temperature under nitrogen. The resultant mixture was heated in an oil bath at 45° C. for 4 hr. After concentration and subsequent flash chromatography on silica (CHCl$_3$), compound 6n was obtained as a white solid. mp 102-103° C.; IR(KBr) 3281, 1701, 1664, 1533 cm$^{-1}$; $^1$H-NMR (DMSO-d$_6$) δ1.19 (d, J=6.9 Hz, 6H), 2.38 (s, 3H), 3.30 (h, J=6.9 Hz, 1H), 4.60 (d, J=5.1 Hz, 2H), 7.04-7.07 (m, 1H), 7.18-7.21 (m, 2H), 7.46 (t, J=8.1 Hz, 1H), 7.77 (t, J=7.7Hz, 1H), 7.88 (d, J=8.1 Hz, 1H), 8.01 (d, J=8.1 Hz, 1H), 8.85 (br t, J=5.1 Hz, 1H); ESIMS m/e 341 (M$^+$+1).

Elemental Analyses for $C_{19}H_{20}N_2O_2S.0.2H_2O$: Calculated: C, 66.33; H, 5.98; N, 8.14 Found: C, 66.41; H, 5.75; N, 8.17

EXAMPLE 15

The preparation of 3-Oxo-3H-benzo[d]isothiazole-2-carboxylic acid phenethylamide

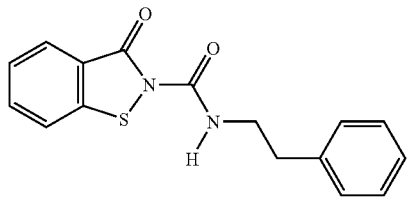

6o

Following the synthetic procedure of 6n as described in Example 14, compound 6o (82% yield) was prepared as a white solid. mp 153-155° C.; IR(KBr) 3282, 1687, 1658 cm$^{-1}$; $^1$H-NMR (DMSO-d$_6$) δ2.86 (t, J=7.2 Hz, 2H), 3.54-3.60 (m, 2H), 7.19-7.33 (m, 5H), 7.45-7.49 (m, 1H), 7.77 (t, J=8.2 Hz, 1H), 7.92 (d, J=8.2 Hz, 1H), 8.00 (d, J=8.2 Hz, 1H), 8.87 (br t, J=5.7 Hz, 1H); ESIMS m/e 299 (M$^+$+1).

Elemental Analyses for $C_{16}H_{14}N_2O_2S.0.1H_2O$: Calculated: C, 64.02; H, 4.77; N, 9.33 Found: C, 63.90; H, 4.73; N, 9.35

EXAMPLE 16

The preparation of 3-Oxo-3H-benzo[d]isothiazole-2-carboxylic acid (2-thiophen-2-yl-ethyl)-amide

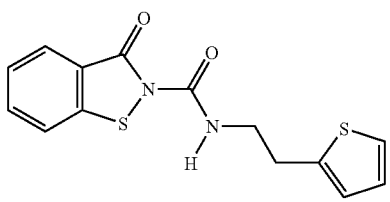

6p

Following the synthetic procedure of 6a as described in Example 1, compound 6p (46% yield) was prepared as a white solid. IR(CHCl$_3$) 3282, 1709, 1665, 1536 cm$^{-1}$; $^1$H-NMR (DMSO-d$_6$) δ3.08 (t, J=7.0 Hz, 2H), 3.55-3.61 (m, 2H), 6.92-6.97 (m, 2H), 7.34 (d, J=5.0 Hz, 1H), 7.47 (t, J=7.6 Hz, 1H), 7.78 (t, J=7.8 Hz, 1H), 7.93 (d, J=7.8 Hz, 1H), 8.01 (d, J=8.0 Hz, 1H), 8.95 (br t, J=5.5 Hz, 1H); ESIMS m/e 305 (M$^+$+1).

Elemental Analyses for $C_{14}H_{12}N_2O_2S_2.0.1H_2O$: Calculated: C, 54.92; H, 4.02; N, 9.15 Found: C, 54.70; H, 3.87; N, 9.13

EXAMPLE 17

The preparation of 3-Oxo-3H-benzo[d]isothiazole-2-carboxylic acid (3-phenyl-propyl)-amide

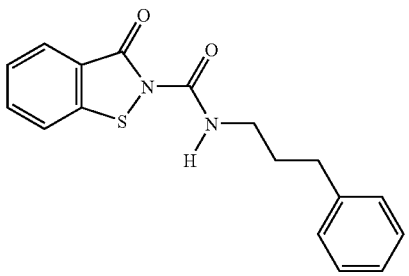

6q

A. The preparation of (3-Isocyanato-propyl)-benzene

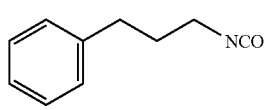

4b'

A solution of 3-phenylpropylamine (345 mg, 2.53 mmol) and proton sponge (1.09 g, 5.10 mmol) in anhydrous CH$_2$Cl$_2$ (5 mL) was added dropwise to a stirred solution of triphosgene (302 mg, 1.02 mmol) in anhydrous CH$_2$Cl$_2$ (5 mL) at 0° C. The resultant solution was allowed to stir at ambient temperature for 15 minutes. After dilution with CH$_2$Cl$_2$ (30 mL), the mixture was washed with 1N HCl (10×2 mL) and water (10 mL). The organic layer was dried over Na$_2$SO$_4$, filtered and concentrated to give the desired isocyanate 4b' (318 mg, 77% yield) as oil. $^1$H-NMR (CDCl$_3$) δ1.57-1.98 (m, 2H), 2.70-2.75 (m, 2H), 3.29-3.34 (m, 2H), 7.17-7.34 (m, 5H).

B. The preparation of 3-Oxo-3H-benzo[d]isothiazole-2-carboxylic acid (3-phenyl-propyl)-amide

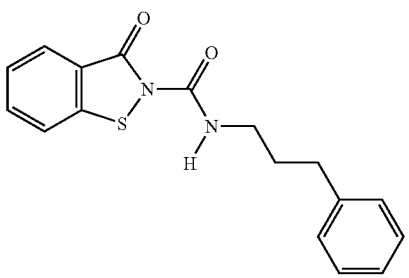

6q

Isocyanate 4b' (318 mg, 1.97 mmol) was added to a stirred solution of benzo[d]isothiazol-3-one (298 mg, 1.97 mmol) in anhydrous THF (5 mL) at ambient temperature under nitrogen. The resultant mixture was heated in an oil bath at 45° C. for 3 hr. After concentration and subsequent flash chromatography on silica (CHCl$_3$), 6q (271 mg, 44% yield) was obtained as a white solid. mp 109-111° C.; IR(KBr) 3281, 1720, 1706, 1647, 1526 cm$^{-1}$; $^1$H-NMR (DMSO-d$_6$) δ1:82-1.90 (m, 2H), 2.63 (t, J=7.6 Hz, 2H), 3.30-3.38 (m, 2H), 7.13-7.30 (m, 5H), 7.48 (t, J=7.6 Hz, 1H), 7.78 (t, J=7.6 Hz, 1H), 7.94 (d, J=7.8 Hz, 1H), 8.01 (d, J=8.2 Hz, 1H), 8.89 (br t, J=5.7 Hz, 1H); ESIMS m/e 313 (M$^+$+1).

Elemental Analyses for C$_{17}$H$_{16}$N$_2$O$_2$S.0.2H$_2$O: Calculated: C, 64.62; H, 5.23; N, 8.87 Found: C, 64.52; H, 4.96; N, 8.77

EXAMPLE 18

The preparation of 3-Oxo-3H-benzo[d]isothiazole-2-carboxylic acid (4-phenyl-butyl)-amide

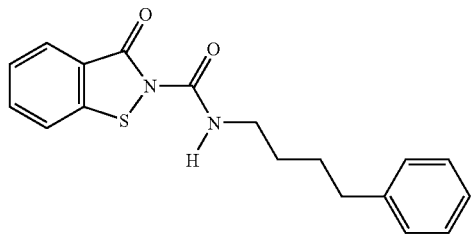

6r

A. The preparation of (4-Isocyanato-butyl)-benzene

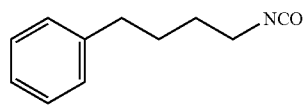

4c'

Following the synthetic procedure of 4b' as described in Example 17, isocyanate 4c' (84% yield) was synthesized from 4-(phenyl)butylamine as an oil. $^1$H-NMR (CDCl$_3$) δ1.61-1.78 (m, 4H), 2.66 (t, J=7.5 Hz, 2H), 3.32 (t, J=6.5 Hz, 2H), 7.17-7.23 (m, 3H), 7.26-7.32 (m, 2H).

B. The preparation of 3-Oxo-3H-benzo[d]isothiazole-2-carboxylic acid (4-phenyl-butyl)-amide

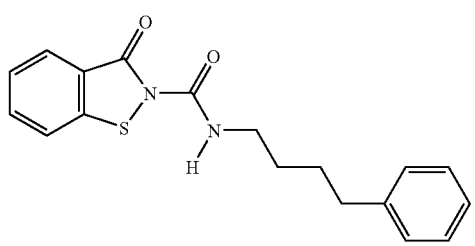

6r

Following the synthetic procedure of 6q as described in Example 17, compound 6r (49% yield) was synthesized from benzo[d]isothiazol-3-one and 4c' as a white solid. mp 119-120° C.; IR(KBr) 3275, 1704, 1690, 1661 cm$^{-1}$; $^1$H-NMR (DMSO-d$_6$) δ1.52-1.65 (m, 4H), 2.60 (t, J=7.0 Hz, 2H), 3.30-3.37 (m, 2H), 7.12-7.30 (m, 5H), 7.48 (t, J=7.6 Hz, 1H), 7.77 (t, J=7.6 Hz, 1H), 7.92 (d, J=7.8 Hz, 1H), 8.00 (d, J=8.2 Hz, 1H), 8.82-8.90 (m, 1H); ESIMS m/e 327 (M$^+$+1).

Elemental Analyses for C$_{18}$H$_{18}$N$_2$O$_2$S.0.1H$_2$O: Calculated: C, 65;87; H, 5.59; N, 8.54 Found: C, 65.70; H, 5.28; N, 8.53

EXAMPLE 19

The preparation of 3-Oxo-3H-benzo[d]isothiazole-2-carboxylic acid (4-cyclohexyl-butyl)-amide

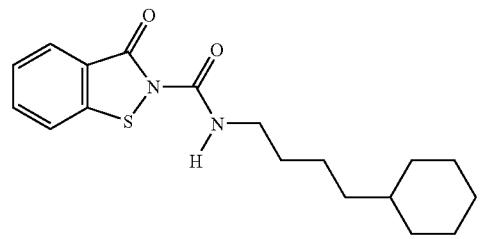

6s

A. The preparation of (4-Isocyanato-butyl)-cyclohexane

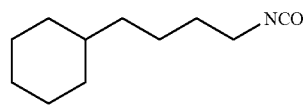

4d'

Following the synthetic procedure of 4b' as described in Example 17, isocyanate 4d' (91% yield) was synthesized from 4-(cyclohexyl)butylamine as an oil. $^1$H-NMR (CDCl$_3$) δ0.80-0.95 (m, 2H), 1.10-1.30 (m, 6H), 1.32-1.45 (m, 2H), 1.52-1.75 (m, 7H), 3.28 (t, J=6.6 Hz, 2H).

B. The preparation of 3-Oxo-3H-benzo[d]isothiazole-2-carboxylic acid (4-cyclohexyl-butyl)-amide

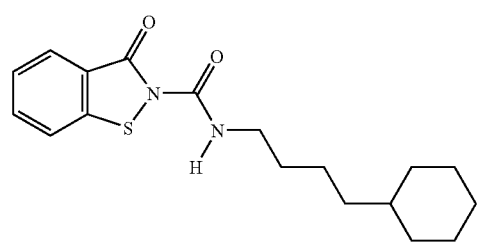

6s

Following the synthetic procedure of 6q as described in Example-17, compound 6s (36% yield) was synthesized from benzo[d]isothiazol-3-one and 4d' as a white solid. mp 76-78°

C.; IR(KBr) 3289, 1711, 1662, 1539 cm$^{-1}$; $^1$H-NMR (DMSO-d$_6$) δ0.75-0.90 (m, 2H), 1.05-1.37 (m, 8H), 1.45-1.72 (m, 7H), 3.30 (t, J=6.7 Hz, 2H), 7.48 (t, J=7.6 Hz, 1H), 7.78 (t, J=7.6 Hz, 1H), 7.93 (d, J=7.8 Hz, 1H), 8.00 (d, J=8.2 Hz, 1H), 8.82-8.86 (m, 1H); ESIMS m/e 333 (M$^+$+1).

Elemental Analyses for C$_{18}$H$_{24}$N$_2$O$_2$S: Calculated: C, 65.03; H, 7.28; N, 8.43 Found: C, 64.87; H, 7.20; N, 8.37

EXAMPLE 20

The preparation of 5-Methyl-3-oxo-3H-benzo[d]isothiazole-2-carboxylic acid butylamide

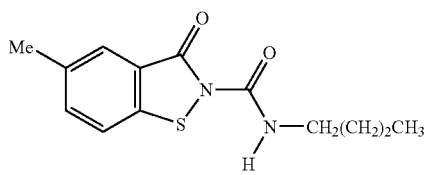

6t

Following the synthetic procedure of 6a as described in Example 1, compound 6t (98% yield) was synthesized from 5-methyl-benzo[d]isothiazol-3-one and n-butyl isocyanate as a white solid. IR(KBr) 3268, 1708, 1650, 1534 cm$^{-1}$; $^1$H-NMR (CDCl$_3$) δ0.96 (t, J=7.3 Hz, 3H), 1.38-1.48 (m, 2H), 1.60-1.67 (m, 2H), 2.46 (s, 3H), 3.41-3.47.(t, 2H), 7.46 (d, J=7.8 Hz, 1H), 7.51 (d, J=7.8 Hz, 1H), 7.80 (s, 1H), 8.88 (br s, 1H); ESIMS m/e 265 (M$^+$+1).

EXAMPLE 21

The preparation of 6-Chloro-3-oxo-3H-benzo[d]isothiazole-2-carboxylic acid propylamide

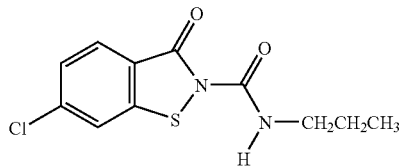

6u

Following the synthetic procedure of 6a as described in Example 1, compound 6u (96% yield) was synthesized from 6-chloro-benzo[d]isothiazol-3-one and n-propyl isocyanate as a white solid. IR(KBr) 3294, 1709, 1635, 1520 cm$^{-1}$; $^1$H-NMR (CDCl$_3$) δ1.00 (t, J=7.3 Hz, 3H), 1.61-1.71 (m, 2H), 3.38-3.44 (m, 2H), 7.38 (d, J=8.8 Hz, 1H), 7.58 (s, 1H), 7.93 (d, J=8.8 Hz, 1H), 8.79 (br s, 1H); ESIMS m/e 271 and 273 (M$^+$+1, $^{35}$Cl and $^{37}$Cl).

Elemental Analyses for C$_{11}$H$_{11}$ClN$_2$O$_2$S: Calculated: C, 48.80; H, 4.10; N, 10.35 Found: C, 48.41; H, 3.85; N, 10.07

EXAMPLE 22

The preparation of 6-Chloro-3-oxo-3H-benzo[d]isothiazole-2-carboxylic acid isopropylamide

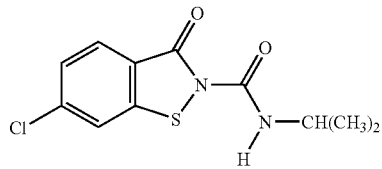

6v

Following the synthetic procedure of 6a as described in Example 1, compound 6v (98% yield) was synthesized from 6-chloro-benzo[d]isothiazol-3-one and iso-propyl isocyanate as a white solid. IR(CHCl$_3$) 3294, 1712, 1533 cm$^{-1}$; $^1$H-NMR (CDCl$_3$) δ1.29 (d, J=6.8 Hz, 6H), 4.12 (hep, J=6.8 Hz, 1H), 7.38 (d, J=8.3 Hz, 1H), 7.58 (s, 1H), 7.92 (d, J=8.2 Hz, 1H), 8.65 (br s, 1H); ESIMS m/e 271 and 273 (M$^+$+1, $^{35}$Cl and $^{37}$Cl).

Elemental Analyses for C$_{11}$H$_{11}$C$_{11}$N$_2$O$_2$S: Calculated: C, 48.80; H, 4.10; N, 10.35 Found: C, 48.71; H, 3.92; N, 10.01

EXAMPLE 23

The preparation of 6-Chloro-3-oxo-3H-benzo[d]isothiazole-2-carboxylic acid butylamide

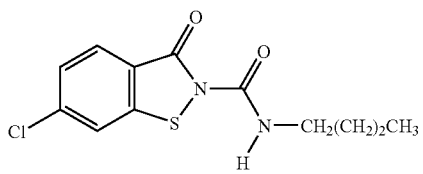

6w

Following the synthetic procedure of 6a as described in Example 1, compound 6w (90% yield) was synthesized from 6-chloro-benzo[d]isothiazol-3-one and n-butyl isocyanate as a white solid. IR(CHCl$_3$) 3294, 1713, 1540 cm$^{-1}$; $^1$H-NMR (DMSO-d$_6$) δ0.89 (t, J=7.3 Hz, 3H), 1.26-1.37 (m, 2H), 1.47-1.55 (m, 2H), 3.28-3.34 (m, 2H), 7.50 (d, J=8.3 Hz, 1H), 7.91 (d, J=8.3 Hz, 1H), 8.14 (s, 1H), 8.76 (t, J=5.6 Hz, 1H); ESIMS m/e 284 and 286 (M$^+$+1, $^{35}$Cl and $^{37}$Cl).

Elemental Analyses for $C_{12}H_{13}ClN_2O_2S$: Calculated: C, 50.61; H, 4.60; N, 9.84 Found: C, 50.70; H, 4.54; N, 9.78

EXAMPLE 24

The preparation of 6-Chloro-3-oxo-3H-benzo[d]isothiazole-2-carboxylic acid hexylamide

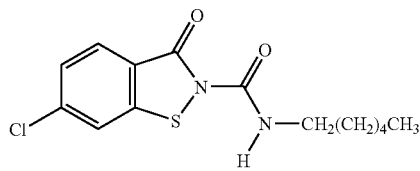

6x

Following the synthetic procedure of 6a as described in Example I, compound 6x (91% yield) was synthesized from 6-chloro-benzo[d]isothiazol-3-one and n-hexyl isocyanate as a white solid. IR(CHCl$_3$) 3298, 1713, 1539 cm$^{-1}$; $^1$H-NMR (CDCl$_3$) δ0.89 (t, J=6.8 Hz, 3H), 1.28-1.43 (m, 6H), 1.60-1.68 (m, 2H), 3.40-3.46 (m, 2H), 7.38 (d, J=8.8 Hz, 1H), 7.58 (s, 1H), 7.93 (d, J=8.8 Hz, 1H), 8.77 (s, 1H); ESIMS m/e 313 and 315 (M$^+$+1, $^{35}$Cl and $^{37}$Cl).

Elemental Analyses for $C_{14}H_{17}ClN_2O_2S$: Calculated: C, 53.75; H, 5.48; N, 8.96 Found: C, 53.67; H, 5.50; N, 8.80

EXAMPLE 25

The preparation of 6-Chloro-3-oxo-3H-benzo[d]isothiazole-2-carboxylic acid cyclohexylamide

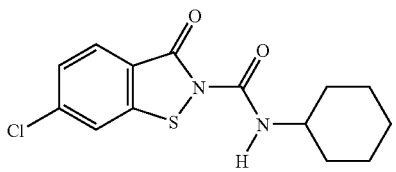

6y

Following the synthetic procedure of 6a as described in Example 1, compound 6y (84% yield) was synthesized from 6-chloro-benzo[d]isothiazol-3-one and cyclohexyl isocyanate as a white solid. IR(CHCl$_3$) 3289, 1711, 1533 cm$^{-1}$; $^1$H-NMR (CDCl$_3$) δ1.20-1.48 (m, 5H), 1.58-1.68 (m, 1H), 1.70-1.80 (m, 2H), 1.92-2.05 (m, 2H), 3.80-3.92 (m, 1H), 7.38 (d, J=8.3 Hz, 1H), 7.58 (s, 1H), 7.92 (d, J=8.3 Hz, 1H), 8.75 (d, J=7.8 Hz, 1H); ESIMS m/e 311 and 313 (M$^+$+1, $^{35}$Cl and $^{37}$Cl).

Elemental Analyses for $C_{14}H_{15}ClN_2O_2S \cdot 0.1H_2O$: Calculated: C, 53.79; H, 4.90; N, 8.96 Found: C, 53.60; H, 4.64; N, 8.77

EXAMPLE 26

The preparation of 6-Chloro-3-oxo-3H-benzo[d]isothiazole-2-carboxylic acid benzylamide

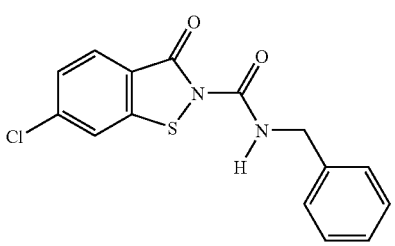

6z

Following the synthetic procedure of 6a as described in Example 1, compound 6z (95% yield) was synthesized from 6-chloro-benzo[d]isothiazol-3-one and benzyl isocyanate as a white solid. IR(CHCl$_3$) 3289, 1713, 1536 cm$^{-1}$; $^1$H-NMR (CDCl$_3$) δ4.63 (d, J=5.8 Hz, 2H), 7.22-7.40 (m, 6H), 7.58 (s, 1H), 7.92 (d, J=8.8 Hz, 1H), 9.15 (br s, 1H); ESIMS m/e 319 and 321 (M$^+$+1, $^{35}$Cl and $^{37}$Cl).

Elemental Analyses for $C_{15}H_{11}ClN_2O_2S$: Calculated: C, 56.52; H, 3.48; N, 8.79 Found: C, 56.38; H, 3.21; N, 8.73

We claim:
1. A benzisothiazole-3(2H)-one compound of formula (I)

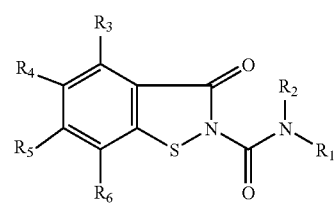

(I)

wherein;
R$_1$ is the group (C$_4$-C$_{12}$)haloalkyl, —CF$_3$, (C$_1$-C$_8$)alkylcycloalkyl, or (C$_3$-C$_8$)cycloalkyl;

R$_2$ is hydrogen;

R$_3$, R$_4$, R$_5$, and R$_6$, are each independently selected from hydrogen, (C$_1$-C$_4$)alkyl, (C$_2$-C$_4$)alkenyl, —O—(C$_1$-C$_3$ alkyl), COOH, C(O)(C$_1$-C$_3$ alkyl), C(O)O(C$_1$-C$_3$ alkyl), —CF$_3$, and halo; or a pharmaceutically acceptable salt thereof.

2. A compound according to claim 1 wherein R$_1$ is (C$_3$-C$_4$) alkylcycloalkyl, or —CF$_3$.

3. The compound of claim 1 wherein R$_5$ is the group represented by chloro, bromo or CF$_3$.

4. A compound selected from the group consisting of:
3-Oxo-3H-benzo[d]isothiazole-2-carboxylic acid allylamide;

Oxo-3H-benzo[d]isothiazole-2-carboxylic acid cyclohexylamide;

3-Oxo-3H-benzo[d]isothiazole-2-carboxylic acid (4-cyclohexyl-butyl)-amide; and

6-Chloro-3-oxo-3H-benzo[d]isothiazole-2-carboxylic acid cyclohexylamide.

5. A pharmaceutical formulation comprising a benzisothiazole-3(2H)-one compound of formula I according to claim 1, or a pharmaceutically acceptable salt thereof, together with a pharmaceutically acceptable carrier or diluent.

6. A method of treating hypercholesterolemia, hyperlipidemia, or atherosclerosis in a mammal in need thereof comprising administering a therapeutically effective amount of benzisothiazole-3(2H)-one compound of formula I, wherein $R_1$-$R_6$ are as defined in claim 1

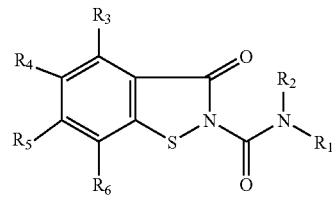

I or a pharmaceutical acceptable salt thereof.

7. The method of claim 6 wherein the benzisothiazole-3(2H)-one compound is formulated with a pharmaceutically acceptable carrier or diluent.

* * * * *